US008742107B1

(12) United States Patent
Rasmussen et al.

(10) Patent No.: US 8,742,107 B1
(45) Date of Patent: Jun. 3, 2014

(54) PROCESS FOR MANUFACTURING BIS(2-METHOXYETHYL)-2,3,6,7-TETRACYANO-1,4,5,8,9,10-HEXA-ZAANTHRACENE

(71) Applicants: Paul George Rasmussen, Ann Arbor, MI (US); Richard Graham Lawton, Ann Arbor, MI (US)

(72) Inventors: Paul George Rasmussen, Ann Arbor, MI (US); Richard Graham Lawton, Ann Arbor, MI (US)

(73) Assignee: Vinazene, Inc., Ann Arbor, MI (US)

( * ) Notice: Subject to any disclaimer, the term of this patent is extended or adjusted under 35 U.S.C. 154(b) by 0 days.

(21) Appl. No.: 13/691,842

(22) Filed: Dec. 2, 2012

(51) Int. Cl.
 *C07D 487/14* (2006.01)
(52) U.S. Cl.
 USPC .......................................................... 544/345
(58) Field of Classification Search
 CPC .................................................... C07D 487/14
 USPC .......................................................... 544/345
 See application file for complete search history.

(56) References Cited

U.S. PATENT DOCUMENTS 3,879,394 A 4/1975 Donald
8,080,327 B1 12/2011 Rasmussen

OTHER PUBLICATIONS

Jae-Yun Jaung, Koushi Fukunishi, Matsaru Matsuoka; "Syntheses and Spectral Properties of 2,3,7,8,-Tetracyano-5,10-dihydrodipyrazino[2,3b:2',3'-e]pyrazine", J. Heterocyclic Chem, Mar.-Apr. 1997, 653-657pp. 34, Japan.
Frances Stöckner, Rainer Beckert, Dieter Gleich, Eckhard Birckner, Wolfgang Günther, Helmar Görls, and Gavin Vaughan; Polyazaacenes—On the Way to Stable, Fluorescent and Redox-Active Derivatives; Eur. J. Organic Chemistry; 2007, 1237-1243pp, Wiley-VCH Verlag GmbH & Co. KGaA, Weinheim, Germany.

*Primary Examiner* — Douglas M Willis
(74) *Attorney, Agent, or Firm* — Jelic Patent Services, LLC; Stanley E. Jelic

(57) ABSTRACT

A process to manufacture substituted tetracyano-hexaazatricyclics with the substitutions occurring at the 9 and 10 hydrogens. The process begins with 2,3-dichloro-5,6-dicyanopyrazine, which is reacted to form the desired tetracyano-hexaazatricyclic. Different process embodiments enable different reaction paths to the desired tetracyano-hexaazatricyclic. Different tetracyano-hexaazatricyclic embodiments include bis(2-methoxyethyl)-2,3,6,7-tetracyano-1,4,5,8,9,10-hexazaanthracene and bis(2-methoxyethoxyethyl)-2,3,6,7-tetracyano-1,4,5,8,9,10-hexazaanthracene.

2 Claims, 10 Drawing Sheets

PROCESS FOR MANUFACTURING BIS(2-METHOXYETHYL)-2,3,6,7-TETRACYANO-1,4,5,8,9,10-HEXAAZAANTHRACENE

STATEMENT REGARDING FEDERALLY SPONSORED RESEARCH OR DEVELOPMENT

This invention was made with government support under DE-SC0007662 awarded by the Department of Energy. The government has certain rights in this invention.

BACKGROUND OF THE INVENTION

Substituted tetracyano-hexaazatricyclics have significant potential use in the electrochemical area. This is due to the high redox capability of the molecules. Potential applications are discussed in further detail in U.S. Pat. No. 8,080,327 (Rasmussen).

FIELD OF THE INVENTION

The present disclosure relates to chemical processes used to make substituted tetracyano-hexaazatricyclics. More particularly, to processes where the tetracyano-hexaazatricyclics are substituted at the 9 and 10 positions.

BRIEF SUMMARY OF THE INVENTION

The present disclosure discusses a process to manufacture substituted tetracyano-hexaazatricyclics, with the substitutions occurring at the 9 and 10 hydrogens. The process comprises reacting 2,3-dichloro-5,6-dicyanopyrazine and, in a series of steps, manufacturing the desired tetracyano-hexaazatricyclic embodiment, wherein the embodiment has substitutions occurring at the 9 and 10 hydrogens.

The scope of the invention is defined by the claims, which are incorporated into this section by reference. A more complete understanding of embodiments on the present disclosure will be afforded to those skilled in the art, as well as the realization of additional advantages thereof, by consideration of the following detailed description of one or more embodiments. Reference will be made to the appended sheets of drawings that will first be described briefly.

The following detailed description of the invention is merely exemplary in nature and is not intended to limit the invention or the application and uses of the invention. Furthermore, there is no intention to be bound by any theory presented in the preceding background of the invention or the following detailed description of the invention.

DETAILED DESCRIPTION OF THE INVENTION

Figure 1:
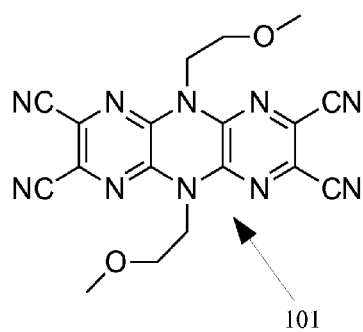
FIG. 1 is a depiction of bis(2-methoxyethyl)-2,3,6,7-tetracyano-1,4,5,8,9,10-hexazaanthracene.
Figure 2:
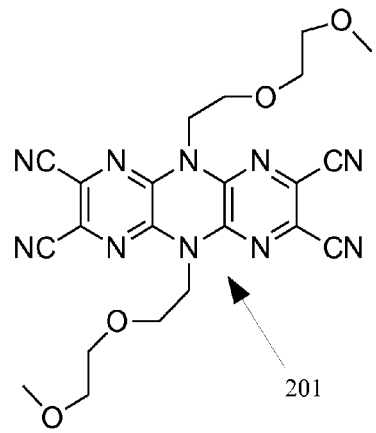
FIG. 2 is a depiction of bis(2-methoxyethoxyethyl)-2,3,6,7-tetracyano-1,4,5,8,9,10-hexazaanthracene.

The present disclosure discusses the manufacturing of the molecules shown in FIG. 1 bis(2-methoxyethyl)-2,3,6,7-tetracyano-1,4,5,8,9,10-hexazaanthracene 101 and FIG. 2 bis(2-methoxyethoxyethyl)-2,3,6,7-tetracyano-1,4,5,8,9,10-hexazaanthracene 201. The goal is to manufacture molecules 101 and 201 through practical, direct, and straightforward pathways that could be expanded for multi-gram scale production. Molecules of this type had been previously manufactured but only on small scale with simple alkyl substitution and never with oxygen functionality.

Figure 3:
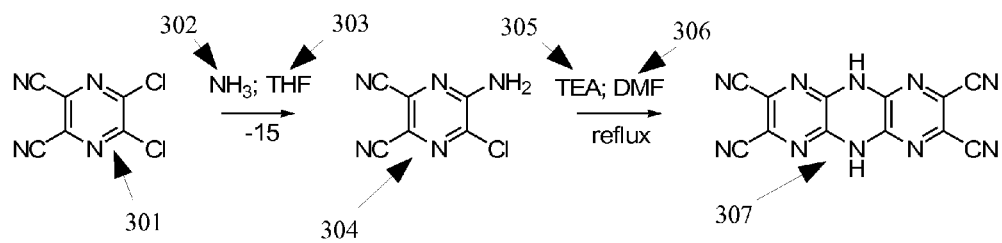
FIG. 3 is an embodiment of the reaction steps used to make tetracyanohexaazaanthracene.

FIG. 3 shows how the core structure of the desired tetracyanohexaazaanthracene 307 framework had previously been manufactured. The process begins with 2,3-dichloro-5,6-dicyanopyrazine 301 which is reacted in a ammonia NH3 302 and tetrahydrofuran THF 303 mixture at 15 degrees Celsius; through dimerization of 2-amino-3-chloro-5,6-dicyanopyrazine 304 in refluxing dimethylformamide [DMF] 306 using triethylamine 305 to pick up the eliminated HCl; however the yields were always poor [J. Juang, K. Fukunishi and M. Matsuoka J. Heterocyclic Chem., 34. 653 (1997)].

Figure 4:
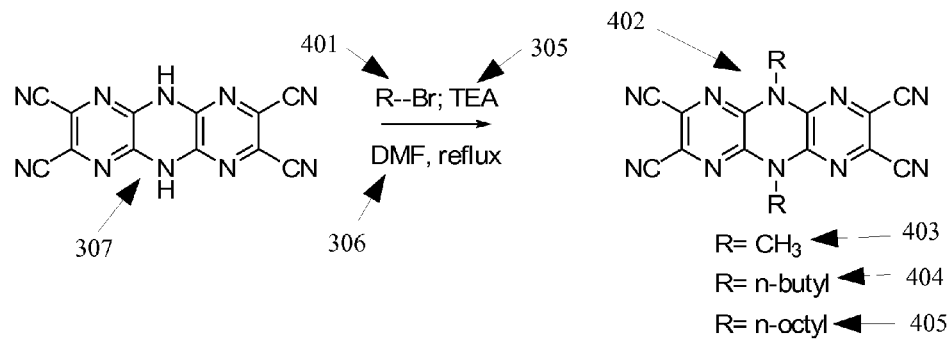
FIG. 4 is an embodiment of the reaction steps used to make substituted tetracyanohexaazaanthracene.
Figure 5:
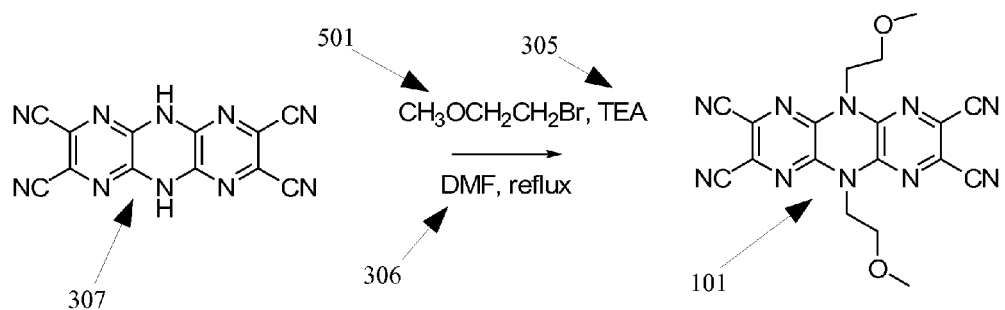
FIG. 5 is an embodiment of the traditional reaction steps used to make bis(2-methoxyethyl)-2,3,6,7-tetracyano-1,4,5,8,9,10-hexazaanthracene.
Figure 6:
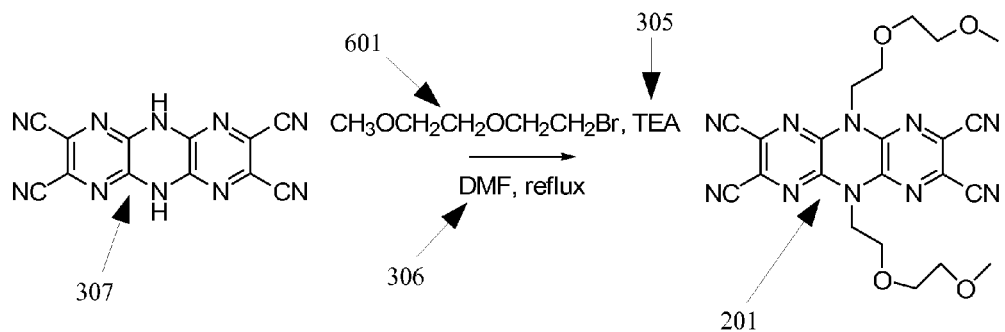
FIG. 6 is an embodiment of the traditional reaction steps used to make bis(2-methoxyethoxyethyl)-2,3,6,7-tetracyano-1,4,5,8,9,10-hexazaanthracene.

Following the synthesis of the 307, FIG. 4 shows that substitution of both the 9 & 10 hydrogens with alkyl groups had previously been accomplished using the corresponding alkyl bromide 401 in refluxing DMF 306 solvent—again using triethylamine 305 to absorb HCl, though again in poor yield. Very large molar excesses of the alkyl bromide 401 were also necessary, the temperature was high [DMF reflux; 160° C.] and the reflux period was several days. Substituted root tetracyanohexaazaanthracene 402 is shown with R embodiments represented as CH3 403, n-butyl 404, and n-octyl 405. These characteristics suggested the construction of compounds 101 and 201 would not be simple and application to large scale might be problematic.

To explore the synthetic paths to both the bis(2-methoxyethyl) derivative 101 and bis(2-methoxyethoxyethyl) derivative 201, we accomplished the traditional sequence by first construction of dicyano-dichloropyrazine 304, converting this to core framework 307 and then using alkylation of 307 with 2-methoxyethyl bromide [$CH_3$—O—$CH_2CH_2$—Br] 501 in DMF 306/TEA 305 giving 101 and 2(2-methoxyethoxy)ethyl bromide [$CH_3$—O—$CH_2CH_2$—O—$CH_2CH_2$—Br] 601 in DMF 306/TEA 305 giving 202. The synthesis was productive but yields were, as expected, very low. Also, the synthetic process was tedious and expensive because both reagents are expensive and need to be used in 10-20 fold excess to give reasonable reaction rates. Further, even with excess alkylating reagents the sequence required two long heating periods; the first for the conversion of pyrazine 304 to tricyclic 307 and the second alkylation of 307 to give 101 or 201. Note that the process cannot easily be separated, though there are two sequential steps. Once 307 is produced, its transformation to 101 starts to proceed.

Figure 7:
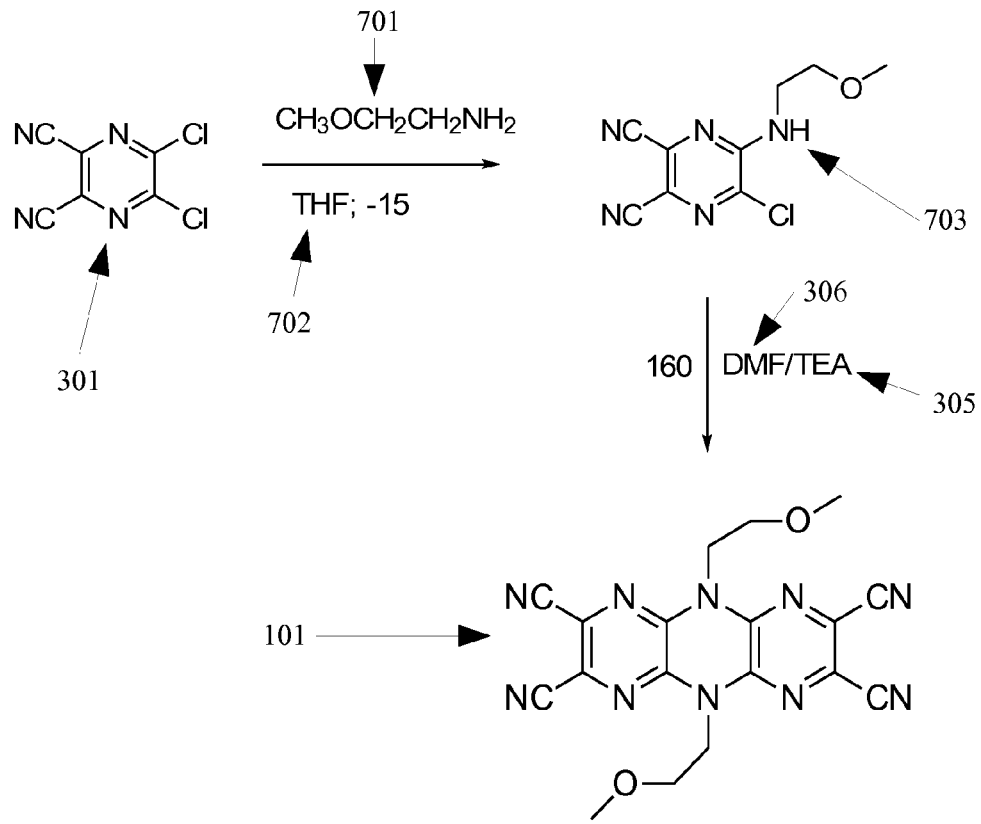
FIG. 7 is an embodiment of the reaction steps used to make bis(2-methoxyethyl)-2,3,6,7-tetracyano-1,4,5,8,9,10-hexazaanthracene.

The present disclosure explores an alternative, as shown in FIG. 7. Rather than prepare the simple dicyano-amino-chloropyrazine 304, we elected to construct the now substituted 5,6-dicyano-2-methoxyethylamino-3-chloropyrazine 703 using 2-methoxyethylamine 701 in place of ammonia in tetrahydrofuran (THF) 702 at −15. The very high reactivity of the halogens of 301 provided the very nicely crystalline derivative 703 in yields of 80% as a single bright blue fluorescent spot on thin layer chromatography (TLC) or using column chromatography. Upon refluxing derivative 703 in DMF 306/TEA 305 for 6-8 hours, 101 was afforded in only very modest yield. Never-the-less, the two long heating steps had been converted to one.

Figure 8:
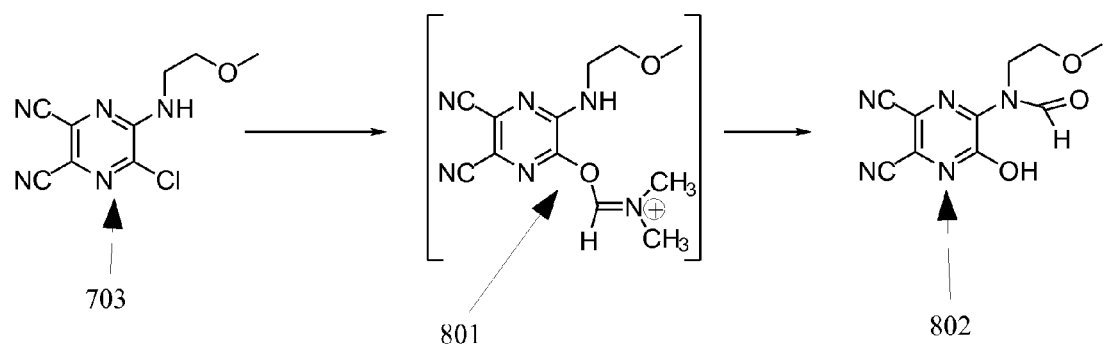
FIG. 8 is an embodiment of the reaction steps used to make hydroxypyrazine.

As we monitored the progress of the conversion of 703 into 101 using TLC or column chromatography, it was noted that a significant new non-fluorescent spot appeared in addition to the bright yellow spot of tricyclic 101. Isolation of this material and determination of it's mass spectrum showed the formation of a material eventually identified as hydroxypyrazine 802, as shown in FIG. 8. Also shown is hydroxypyrazine intermediate 801. Clearly, the DMF 306 solvent had intervened in the reaction and DMF 306 was competing for the reactive halogen of 703 rather than allowing the dimerization of 703 to 101. This intervention was clearly the reason for the low yields in the conversion of 703 to 101.

Figure 9:
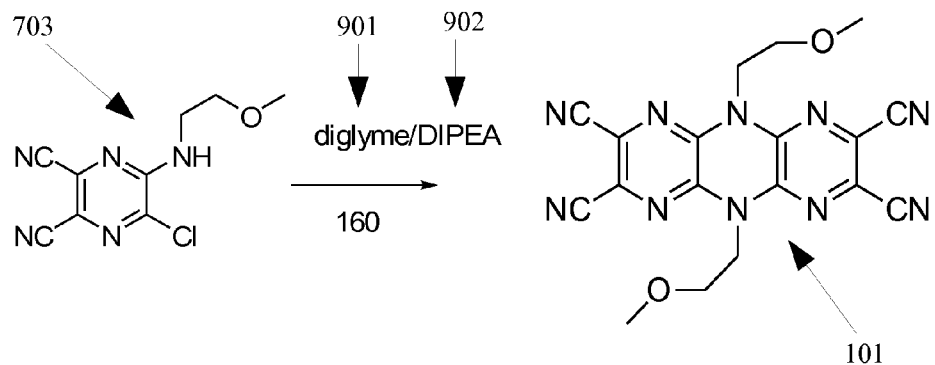
FIG. 9 is an embodiment of a final reaction step used to make bis(2-methoxyethyl)-2,3,6,7-tetracyano-1,4,5,8,9,10-hexazaanthracene.

Thus, we explored many numerous alternative solvents including other amide solvents such as N-methylpyrrolidone, dimethylacetamide. FIG. 9 shows the discovered reaction pathway: diglyme [$CH_3$—O—$CH_2CH_2$—O—$CH_2CH_2$—$OCH_3$; diethyleneglycol dimethyl ether; bp 160] 901 and diisopropylethylamine [DIPEA] 902 was an excellent medium and solvent to accomplish the transformation of 703 to 101. Refluxing pyrazine 703 in diglyme 901 with DIPEA 902 afforded good [60-70%] yields of substituted tricyclic 101. The reaction can be followed easily by TLC or column chromatography and isolation by cooling to room temperature and upon pouring the reaction mix into ice/water, a brownish-yellow-orange solid precipitates almost pure without chromatography. This material has been used extensively in our CV and charge/discharge experiments.

Figure 10:
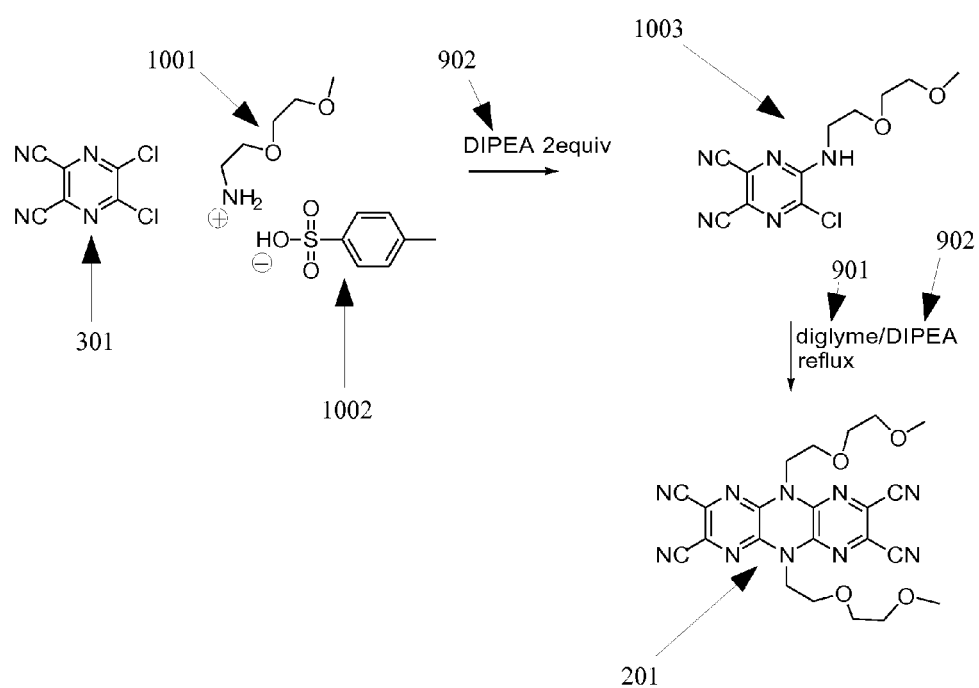
FIG. 10 shows an alternate reaction pathway for the preparation of bis(2-methoxyethoxyethyl)-2,3,6,7-tetracyano-1,4,5,8,9,10-hexazaanthracene.

Though the construction of bis(2-methoxyethyl) tricyclic 101 was accomplished it remained to be determined if a similar sequence could be established for the synthesis of 201. 2-Methoxyethylamine is commercially available inexpensively. The required corresponding 2-methoxyethoxyethylamine is not. Several attempts to synthesize this material failed including the Gabriel synthesis using the phthalimide intermediate. The failure in each attempt involved the very high water solubility of the aminodiether. FIG. 10 shows a new preparation of the required amine 1001 through the construction of the p-toluenesulfonate ester of monoglyme [$CH_3$—O—$CH_2CH_2$—O—$CH_2CH_2$—OH] 1002. Upon treatment of this material with a very large excess of aqueous ammonia at room temperature for several days followed by rotoevaporation of the aqueous solution yields the p-toluenesulfonate salt of 2-methoxyethoxyethylamine 1002. The salt 1002 is taken up in THF and evaporated to remove traces of water by azeotropic processes. The salt 1002 along with dichloropyrazine 301 was dissolved in THF and treated with DIPEA 902 [2 equivalents] at −15° Celsius gave good yields of the corresponding substituted 2-methoxyethoxyethylamino chloro pyrazine 1003. Using the same procedure as in the conversion of 703 to 101 (Refluxing 1003 in diglyme 901 with DIPEA 902 to yield 201), the more highly oxygenated side-chain aminopyrazine 1003 is converted to 201.

Figure 11:
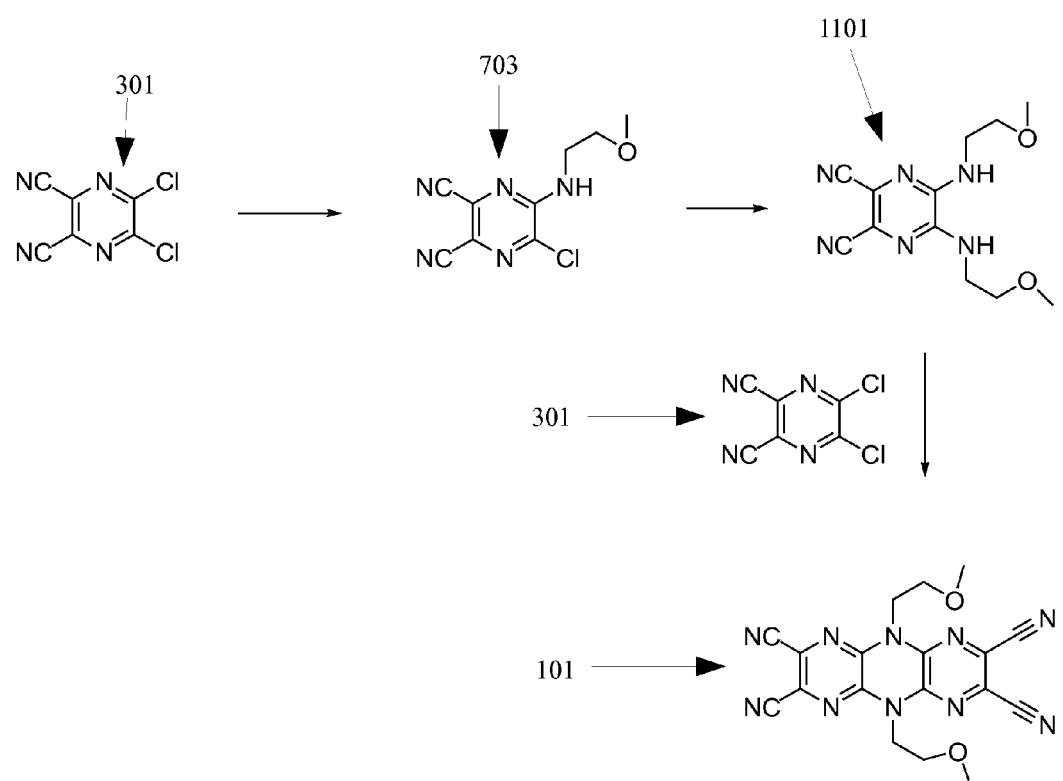
FIG. 11 shows an alternate reaction pathway for the preparation of bis(2-methoxyethoxyethyl)-2,3,6,7-tetracyano-1,4,5,8,9,10-hexazaanthracene.

In order to explore routes that would allow the construction of unsymmetrical derivatives of the tetracyano hexaaza tricyclic we have also explored the combination of a disubstituted diaminopyrazine with the dicyanodichloropyrazine 301, as shown in FIG. 11. In the event, dicyanodichloropyrazine 301 was treated with 2 equivalents of 2-methoxyethylamine 701 (in THF 702 at −15 degrees Celsius) and the substitution of both halogens accomplished in a sequential way to give substituted diaminopyrazine 1101 (703 is shown as an intermediate in FIG. 11). This was then caused to react with dichlorodicyanopyrazine 301 to give the exactly the same tricyclic structure 101 as produced by the dimerization of pyrazine 703. Many other side-chains and derivatives can thus be designed, constructed and explored.

2,3-Dicyano-1,4-dihydro-5,6-diketopyrazine 1204

Figure 12:
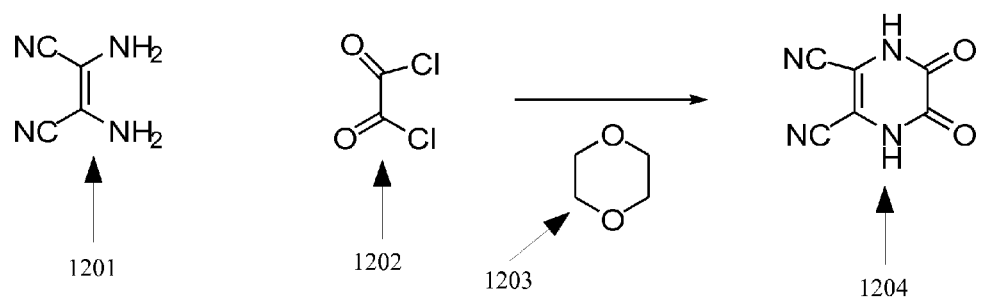
FIG. 12 shows a reaction pathway for the preparation of 2,3-Dicyano-1,4-dihydro-5,6-diketopyrazine.

FIG. 12 shows the reaction pathway. A 500 mL Erlenmeyer flask was charged with a magnetic stir bar and to this setup was introduced 375 mL of anhydrous 1,4-dioxane 1201. The dioxane is cooled in ice/water mixture and after well cooled and with good stirring, 15 mL of oxalyl chloride [171 mmol; d=1.45] 1202 is added slowly. The combination will be exothermic. The mixture is allowed to stand until well chilled and a $N_2$ sweep is established. To the well stirred mixture is added, in small [~2 g or smaller] portions over an hour, a total of 15 g [139 mmol] of purified DAMN 1203 in the solid state. After the last portion is added the flask is sealed with parafilm and stirring continued for ~1 hour followed by then warming in a water bath to 50° C. for some 3-4 hours during which time the solution and thick suspension turned light yellow. The thick suspension is cooled to room temperature and placed in a freezer compartment of a refrigerator [~−20° C.] for about an hour [not longer or dioxane solvent may freeze]. The solid was filtered by suction on a sintered-glass filter, washed with cold ether and dried. The material can be crystallized from boiling water. Yield ~85%.

2,3-Dichloro-5,6-dicyanopyrazine 301

Figure 13:
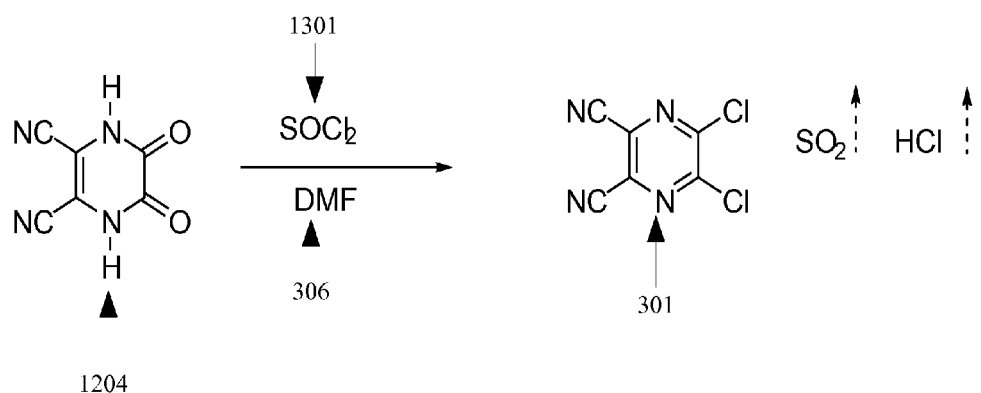
FIG. 13 shows a reaction pathway for the preparation of 2,3-Dichloro-5,6-dicyanopyrazine.

FIG. 13 shows the reaction pathway. This reaction should be carried out in a fume hood. In a 500 mL round-bottomed flask with a 24/40 ground-glass joint attached to an efficient reflux condenser and under a nitrogen atmosphere, a magnetically stirred slurry consisting of 8.10 g (0.050 mol) of 1,4,5,6-tetrahydro-5,6-dioxo-2,3-pyrazinedicarbonitrile, 4.0 mL of dimethylformamide 306 and 160 mL of thionyl chloride 1301 was heated. Gas evolution began at ca. 62° [SO2 & HCl gasses evolved]. After about 3.5 hours, the solid had dissolved and the temperature had risen to 70°. After cooling to room temperature, a Dry Ice/acetone bath was applied until the temperature of the reaction medium was −65°. The crystals which formed were collected by rapid filtration of the cold slurry through a sintered-glass filter under a nitrogen blanket. The solid was washed twice with 150-ml portions of cold diethyl ether and air-dried to give 7 g (70%) of 2,3-dichloro-5,6-dicyanopyrazine 301, mp 180-182°. Crystallization of the product may be accomplished if dark, from ~50 mL of chloroform with carbon treatment to give 5.5 g of purified product.

2-(2-Methoxyethylamino)-3-chloro-5,6-dicyanopyrazine 1401

Figure 14:
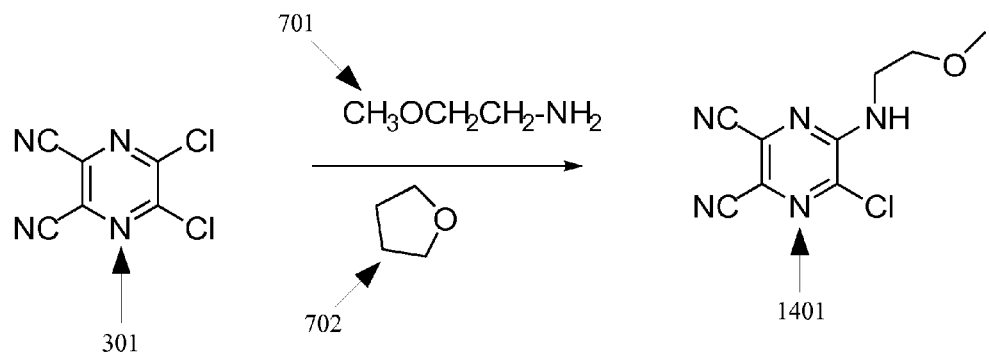
FIG. 14 shows a reaction pathway for the preparation of 2-(2-Methoxyethylamino)-3-chloro-5,6-dicyanopyrazine.

FIG. 14 shows the reaction pathway. A solution of 5.00 g (25.1 mmoles) of 2,3-dichloro-5,6-dicyanopyrazine 301 in 40 mL of anhydrous tetrahydrofuran was cooled to between −15° and −20° [bath temperature] in a Dry Ice/acetone bath and a solution of 3.95 g (52.6 mmoles) of 2-methoxyethylamine 701 in 30 mL of anhydrous tetrahydrofuran 702 was added drop-wise, with good magnetic stirring over a period of about 30 minutes. After warming to ~5° for an additional 15 minutes, the still cold reaction mixture was poured, with good agitation, into 400 mL of ice/water mix having ~5 mL of 10% HCl added, producing an oil which rapidly crystallized to a yellow solid. The solid was filtered, washed well with water and air-dried to give 4.1 g of yellow solid 2-(2-methoxyethylamino)-3-chloro-5,6-dicyanopyrazine 1401, mp 111°.-113°. The product was purified by crystallization from ethyl acetate/hexane to give the purified product as pale yellow crystals, mp 113°-114°. Exact mass 237.1 [calc 237.04] TLC or column chromatography in ethyl acetate on silica plates shows an intense blue fluorescent spot at Rf ~0.65; a trace of the double addition 2,3-bis(2-methoxyethylamino)-5,6-dicyanopyrazine can often be seen at Rf ~0.45. This same process may also be used with 2-(2-methoxyethoxy)ethylamine to afford the more extended derivative.

5,10-bis(2-methoxyethyl)-5,10-dihydrodipyrazino[2,3-b:2',3'-e]pyrazine-2,3,7,8-tetracarbonitrile 101 (also known as bis(2-methoxyethyl)-2,3,6,7-tetracyano-1,4,5,8,9,10-hexazaanthracene)

Figure 15:
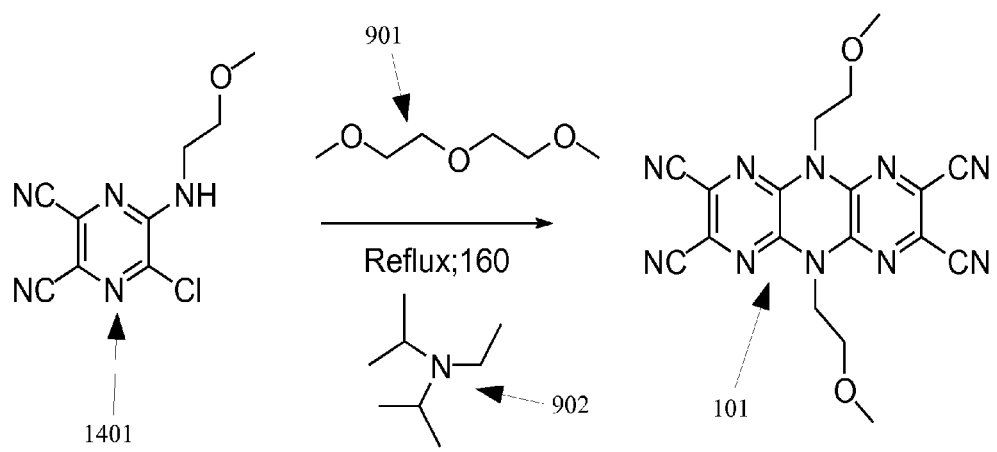
FIG. 15 shows a reaction pathway for the preparation of 5,10-bis(2-methoxyethyl)-5,10-dihydrodipyrazino[2,3-b:2',3'-e]pyrazine-2,3,7,8-tetracarbonitrile.

FIG. 15 shows the reaction pathway. In a 100 mL round-bottom flask with 14/20 glass joint and attached to an air-condenser having a magnetic stir-bar was add 4.8 g [0.02 mole] of 2(2-methoxyethylamino)-3-chloro-5,6-dicyanopyrazine 1401 and 25 mL of diglyme 901 [diethyleneglycol dimethylether]. The reaction was stirred for about an hour until all the solid had dissolved. To this solution was added 6.2 g of diisopropylethylamine 902 drop-wise with stirring. The reaction was then brought to reflux using a sand-bath at ~180° Celsius. All under a nitrogen sweep. The solution acquired an orange yellow color as heating took place. Reaction was monitored by TLC or column chromatography [silica plates] using ethyl acetate; the bright blue fluorescent starting material spot at Rf: 0.65 slowly faded and was converted to a bright yellow spot at Rf: 0.98. After 5 hours the starting material spot had disappeared and the new yellow spot at solvent front in TLC or column chromatography predominated. Solution cooled to rt and poured, with good stirring into 400 mL of water/ice mixture having ~5 mL of 10% HCl. Brown-yellow mixture was allowed to stand ~24 hrs and filtered by suction and washed with water. Material was dried in vac. drying oven at 70°. There was obtained 4.1 g of yellow brown powder. Exact mass 402.2 [calc 402.13].

2,3-bis(2-Methoxyethylamino)-5,6-dicyanopyrazine 1101

Figure 16:
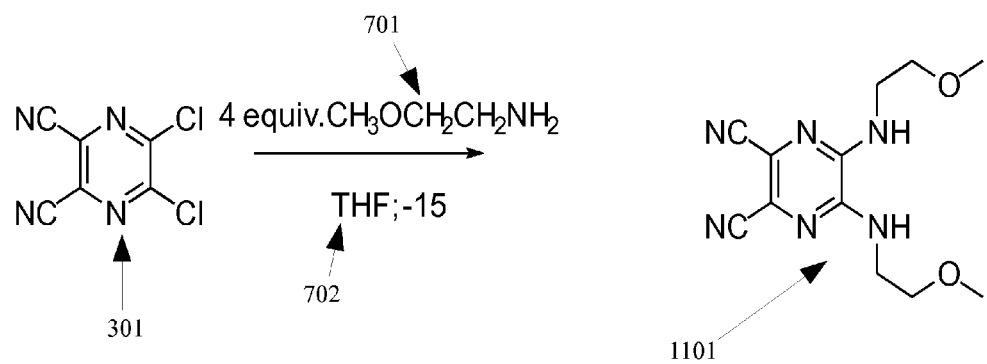
FIG. 16 shows a reaction pathway for the preparation of 2,3-bis(2-Methoxyethylamino)-5,6-dicyanopyrazine.

FIG. 16 shows the reaction pathway. A solution of 5.00 g (25.1 mmoles) of 2,3-dichloro-5,6-dicyanopyrazine 301 in 40 mL of anhydrous tetrahydrofuran 702 was cooled to between −15° and −20° [bath temperature] in a Dry Ice/acetone bath and a solution of 8 g (104 mmoles) of 2-methoxyethylamine 701 in 30 mL of anhydrous tetrahydrofuran 702 was added drop-wise, with good magnetic stirring over a period of about 30 minutes. After warming to ~5° for an additional 15 minutes, the still cold reaction mixture was poured, with good agitation, into 500 mL of ice/water mix having ~5 mL of 10% HCl added, producing an oil which rapidly crystallized to a yellow solid. The solid was filtered, washed well with water and air-dried to give 4.7 g of pale yellow solid 2,3-bis(2-methoxyethylamino)-5,6-dicyanopyrazine 1101. Rf: 0.45 in ethyl acetate on silica plates.

The amount of primary amine can be reduced by half by substituting another amine such as diisopropylethylamine to react with the HCl generated during the reaction. Thus, instead of 8 g of 2-methoxyethylamine 701, one can use 4 g of 2-methoxyethylamine 701 and 5 g diisopropylethylamine mixture in 30 mL THF 702.

5,10-bis(2-methoxyethyl)-5,10-dihydrodipyrazino[2,3-b:2',3'-e]pyrazine-2,3,7,8-tetracarbonitrile 101

Figure 17:
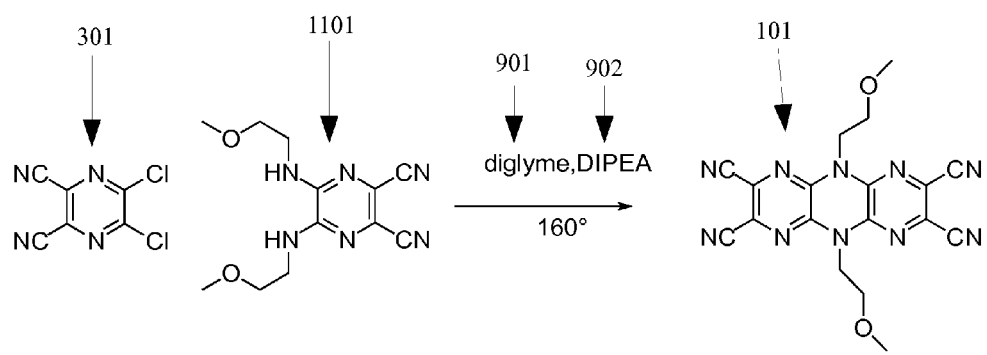
FIG. 17 shows a reaction pathway for the preparation of 5,10-bis(2-methoxyethyl)-5,10-dihydrodipyrazino[2,3-b:2',3'-e]pyrazine-2,3,7,8-tetracarbonitrile.

FIG. 17 shows the reaction pathway. In a 100 mL round-bottom flask having a magnetic stir-bar and with 14/20 glass joint attached to an air-condenser was add 0.48 g [0.002 mole] of 2,3-bis(2-methoxyethylamino)-5,6-dicyanopyrazine 1101, 2,3-dichloro-5,6-dicyanopyrazine 301 and 5 mL of diglyme 901 [diethyleneglycoldimethylether]. The reaction was stirred for about an hour until all the solids had dissolved. To this solution was added 0.6 g of diisopropylethylamine 902 drop-wise with stirring. The reaction was then brought to reflux using a sand-bath at ~180°. All under a nitrogen sweep. The solution acquired a dark gray orange color as heating took place. Reaction was monitored by TLC or column chromatography [silica plates] using ethyl acetate; the bright blue fluorescent starting material spot at Rf: 0.45 slowly faded and was converted to a bright yellow spot at Rf: 0.98 identical to the material formed from dimerization. After 5 hours the starting material spot remained though the yellow spot corresponding to the expected product at solvent front in TLC or column chromatography was present. Solution cooled to rt and poured, with good stirring into 40 mL of water/ice mixture having ~0.5 mL of 10% HCl. Dark mixture was allowed to stand ~24 hrs and filtered by suction and washed with water. Material was dried in vac. drying oven at 70°. There was obtained 0.6 g of yellow brown powder having both starting material and desired tetracyanodipyrazinepyrazine. Exact mass 402.2 [calc 402.13].

2-(2-Methoxyethoxy)ethyl ammonium tosylate salt 1001 and 2-(2-Methoxyethoxy)ethyl p-toluenesulfonate 1002

Figure 18:
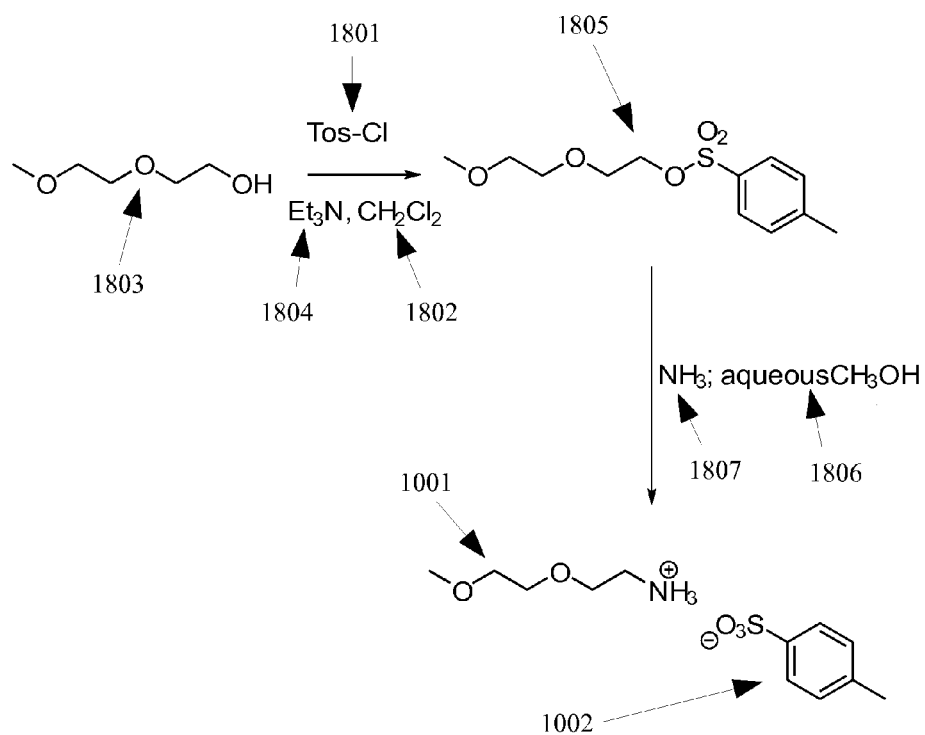
FIG. 18 shows a reaction pathway for the preparation of 2-(2-Methoxyethoxy)ethyl ammonium tosylate salt 1001 and 2-(2-Methoxyethoxy)ethyl p-toluenesulfonate.

FIG. 18 shows the reaction pathway. In a 500 mL Erlenmeyer flask 38 g of p-toluenesulfonyl chloride 1801 was dissolved in 90 mL of dichloromethane 1802 with stirring using a magnetic stirrer. To this solution was added 24 g of 2-(2-methoxyethoxy)ethanol 1803. The solution was cooled in an ice/water mixture and to this clear, cold, slightly yellow solution was added, with good stirring 20.4 g of triethylamine 1804, drop-wise by pipette. The amine 1804 was added over ~20 min. At the end of the addition, crystals of triethylamine hydrochloride had started to deposit from the solution. Reaction was allowed to stir over night. The reaction solution was then poured into ~200 mL of ice/water containing 10 mL of concentrated hydrochloric acid. The mixtures was stirred well, and the organic layer removed by separatory funnel. The aqueous layer was extracted with another 40 mL of dichloromethane 1802 and added to the previous. The combined organic layers were washed with saturated salt solution and dried over anhydrous sodium sulfate. After decanting from $Na_2SO_4$ and roto-evaporation, there was obtained 50.4 g of pale, tan oil. Upon several cooling, warming sequences in a dry-ice/acetone bath while under vacuum, the oil crystallized. The tosylate is a solid at 0° but melts to a syrup at room-temperature. Yield 50.4 g [theory 54 g].

2-(2-Methoxyethoxy)ethyl ammonium tosylate salt

The whole of the 2-(2-methoxyethoxy)ethyl tosylate 1805 [50 g] was dissolved in 100 mL of methanol 1806 and this solution was added with good stirring to 300 mL of concentrated aqueous ammonia 1807 in a 500 mL Erlenmeyer flask. After about ⅔ of the addition, incremental amounts of methanol were required to maintain a clear solution as the methanol/tosylate solution was added. Total volume at the end of the addition was ~500 mL. The reaction flask was covered and allowed to stir for ~4 days. From the beginning of the addition of the tosylate to the ammonia solution, a distinct yellow hue was observed. As the reaction proceeded, this color faded. At the end of the reaction period the clear solution was transferred to a beaker and allowed to stand in the hood to allow ammonia and methanol to evaporate for ~24 hrs. The remaining water/methanol/ammonia was then removed through roto-evaporation and the residual syrup taken up in tetrahydrofuran and the THF/water azeotrope removed successively. Finally the syrup was taken up in THF and filtered from the crystalline residual ammonium tosylate salt [~5 g]. Evaporation of the THF on roto-evaporator yielded 48 g of light tan syrup: 2-(2-methoxyethoxy)ethyl ammonium tosylate salt. Mass Spectral data for both negative 1002 and positive ions 1001 were observed at 171 and 131 respectively.

All patents and publications mentioned in the prior art are indicative of the levels of those skilled in the art to which the invention pertains. All patents and publications are herein incorporated by reference to the same extent as if each individual publication was specifically and individually indicated to be incorporated by reference, to the extent that they do not conflict with this disclosure.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations, and broad equivalent arrangements. o-3-chloropyrazine used in the next step.

We claim:

1. A process for manufacturing bis(2-methoxyethyl)-2,3,6,7-tetracyano-1,4,5,8,9,10-hexazaanthracene, the process comprising:
   refluxing 5,6-dicyano-2-(2-methoxyethyl)amino-3-chloropyrazine in a mixture of diethylene glycol dimethyl ether and N,N-diisopropyl-N-ethylamine.

2. The process of claim 1, wherein refluxing occurs at temperature of 160 to 180 degrees Celsius.

* * * * *